US00PP27419P3

(12) United States Plant Patent
Aguilar Moran

(10) Patent No.: US PP27,419 P3
(45) Date of Patent: Nov. 29, 2016

(54) BANANA PLANT NAMED 'CQB 114'

(50) Latin Name: *Musa acuminata×balbisiana*
Varietal Denomination: CQB 114

(71) Applicant: Chiquita Brands L.L.C.

(72) Inventor: Juan Fernando Aguilar Moran, La Lima (HN)

(73) Assignee: Chiquita Brands L.L.C., Charlotte, NC (US)

( * ) Notice: Subject to any disclaimer, the term of this patent is extended or adjusted under 35 U.S.C. 154(b) by 106 days.

(21) Appl. No.: 14/121,309

(22) Filed: Aug. 18, 2014

(65) Prior Publication Data

US 2016/0050819 P1 Feb. 18, 2016

(51) Int. Cl.
*A01H 5/08* (2006.01)

(52) U.S. Cl.
USPC ..... Plt./160

(58) Field of Classification Search
USPC ..... Plt./160
See application file for complete search history.

*Primary Examiner* — Annette Para

(74) *Attorney, Agent, or Firm* — Kilpatrick Townsend & Stockton LLP

(57) ABSTRACT

'CQB 114' is a hybrid banana variety that has high provitamin A cartenoid content, has resistance to black Sigatoka, and produces very sweet fruit that can be eaten fresh or used in desserts.

3 Drawing Sheets

Genus and species: The variety of this invention is botanically identified as *Musa acuminata×balbisiana* group AAB, AA representing two genomes of *M. acuminata* and B representing one genome of *M. balbisiana.*

Variety denomination: The variety denomination is 'CQB 114'.

BACKGROUND OF THE INVENTION

This invention relates to a new and distinctive hybrid banana variety designated as 'CQB 114'. The new hybrid variety was the result of a field cross performed at Fundacion Hondurena de Investigacion Agricola (FHIA) in 2005 in La Lima, Cortes, Honduras between SH-4001×Pisang Mas (both unpatented). SH-4001 is a tetraploid French plantain (AAAB) with high content of provitamin A carotenoids (pVAC) from the FHIA germplasm collection. The male parent, Pisang Mas is a naturally occurring diploid (AA). Pisang Mas produces small bunches and very sweet-flavored fingers, which are eaten fresh or used as dessert and are sweeter than the common Cavendish banana.

'CQB 114' was selected in 2008 from several first-generation seedlings from the cross between SH-4001× Pisang Mas. It was selected as a triploid hybrid that maintained the productivity, high content of pVAC, and black Sigatoka leaf spot disease-resistance of its SH-4001 female parental line and produced the very sweet-flavored fruit of the male parental variety Pisang Mas.

'CQB 114' was asexually reproduced by corms by the inventor in the Centro Experimental Demostrativo, the experimental farm of FHIA in La Lima, Cortés, Honduras. All plant and fruit characteristics run true to the original selected plant and are identical in all aspects.

BRIEF SUMMARY OF VARIETY DESCRIPTION

'CQB 114' is a hybrid banana variety that has high provitamin A cartenoid content, has resistance to black Sigatoka leaf spot disease, and produces-sweet-flavored fruit that can be eaten fresh or used in desserts; or eaten green when cooked.

BRIEF DESCRIPTION OF THE PHOTOGRAPHS

The Figures depict various characteristics of the 'CQB 114' hybrid banana variety. The colors shown in the photographs are as nearly true as is reasonably possible in color representations of this type.

FIG. 1 shows the typical appearance of a plant.

FIG. 2 shows blotches at the petiole base and a petiole canal leaf.

FIG. 3 shows the shape of a leaf blade base (A) and leaf upper (B) and lower (C) surfaces.

FIG. 4A-B show water suckers (A) and leaves without blotches (B).

FIG. 5 shows a typical fruit bunch.

FIG. 6 shows a male bud.

Figure 7:
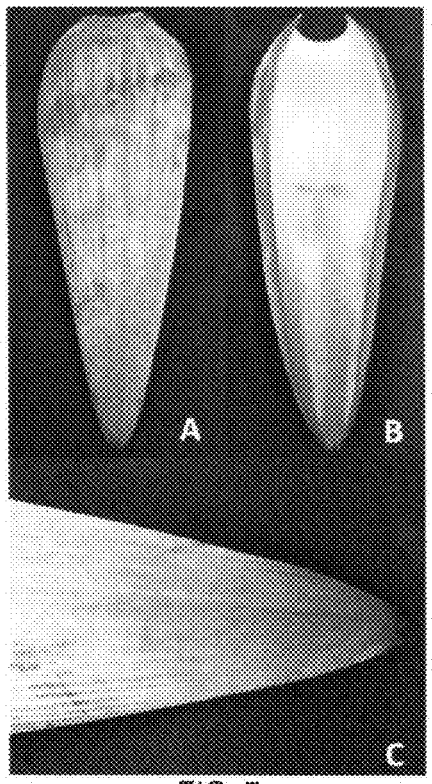

FIG. 7A-C shows bracts of a male bud.

Figures 8A, 8B, 8C:
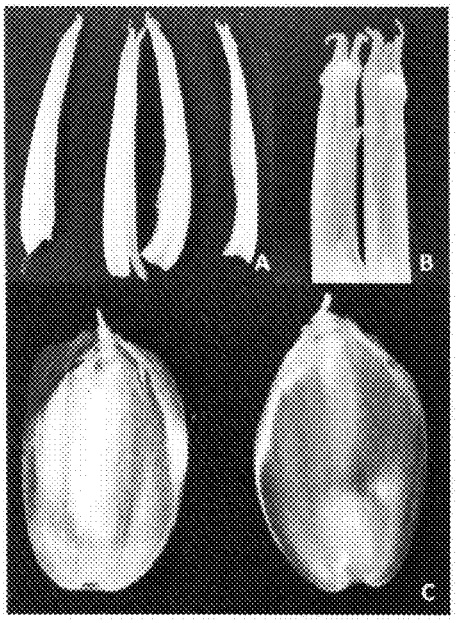

FIG. 8A-C shows lobes of compound tepals (A and B) and a free tepal (C).

Figure 9:
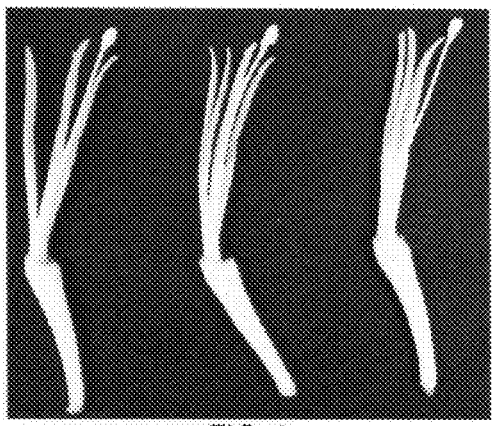

FIG. 9 shows stamens without pollen.

Figure 10A:
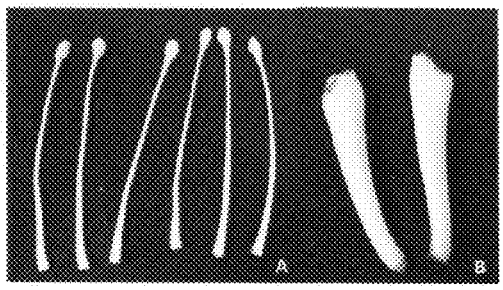

FIG. 10A-B shows the style shape (A) and an ovary (B).

Figure 11:
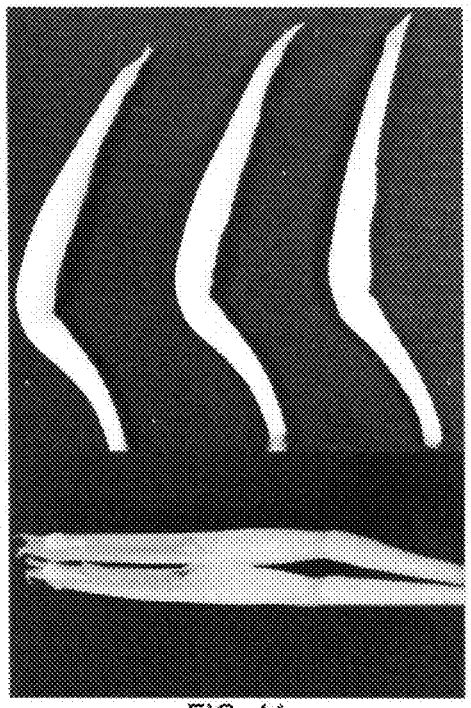

FIG. 11 shows a typical male flower.

Figure 12:
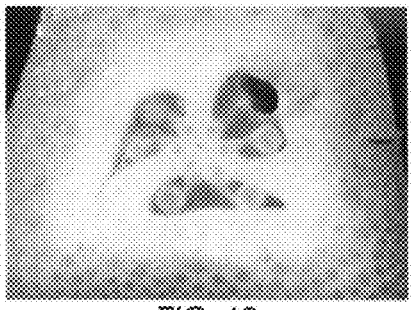

FIG. 12 shows rowed ovules.

Figure 13:
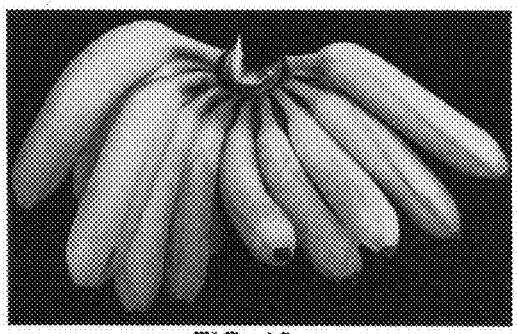

FIG. 13 shows a typical fourth hand.

Figures 14A, 14B, 14C:
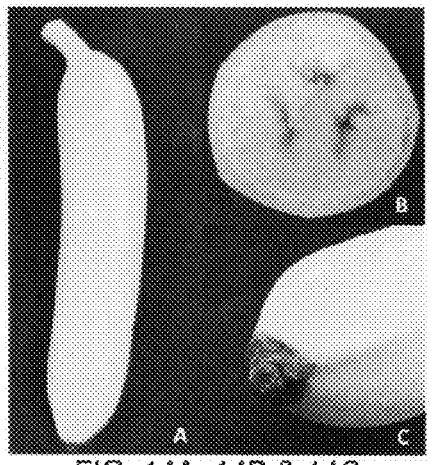

FIG. 14A-C shows the finger shape of a typical mature finger (A); a transverse section of fruit, mature pulp (B); and the fruit apex, mature pulp (C).

DETAILED DESCRIPTION OF THE INVENTION

'CQB 114' differs from its male parent Pisang Mas as follows: 'CQB 114' has higher productivity compared to Pisang Mas, has fingers that are twice as long as those of Pisang Mas, has fingers that are 20% thicker than those of Pisang Mas, has bunches that are 200-300% heavier than those of Pisang Mas, and has a very high content of p-Vac compared to Pisang Mas. In addition, 'CQB 114' is a triploid (3n) AAB whereas Pisang Mas is a diploid (2n) AA.

'CQB 114' differs from its female parent SH-4001 as follows: 'CQB 114' has higher Brix (20 vs 27) compared to SH-4001, has longer shelf live compared to SH-4001, is firmer than SH-4001, and has more fingers of smaller size compared to SH-4001. In addition, 'CQB 114' is a triploid (3n) AAB where as SH-4001 is a 4n AAAB.

'CQB 114' differs from the common Cavandish banana in its high provitamin A cartenoid content and resistance to black Sigatoka leaf spot disease.

The following is a detailed botanical description of the new variety 'CQB 114'. The description is from plants located in Limon, Costa Rica that were evaluated between 2013 and 2014. The Ratooning Index is from data collected in an experimental plot located in El Progreso, Honduras. Colors are described using Munsell Color Chart for Plant Tissues. The descriptions are in accordance with the internationally standardized "Descriptors for Banana (Musa spp.)" elaborated by IPGRI-INIBAP/CIRAD, 1996. Observation were made with bunches that were 90 days old, from 360-day old plants (flowering starts at 270 days).

The 'CQB 114' plant and its fruit may vary slightly from the detailed descriptors shown below due to cultural practices, soil types and climatic conditions under which the variety may be grown.

TABLE 1

| Detailed descriptors |
|---|
| Leaf habit: drooping (FIG. 1) |
| Dwarfism: dwarf type, leaves strongly overlapped and leaf ratio is 3.52 (296/84 cm) |
| Pseudostem height: ≥3.0 m (4.40 to 5.40 m at flowering) |
| Pseudostem aspect: robust (83.0 to 88.0 cm) |
| Pseudostem colour: 2.5GY5/4 |
| Pseudostem appearance: shinny (not waxy) |
| Predominant underlying colour of the pseudostem: 2.5Y8/2 |
| Pigmentation of the underlying pseudostem: 5R4/6 |
| Sap colour: Watery |
| Wax on leaf sheaths: very little or no visible sign of wax |
| Development of suckers: more than ¾ of the height of the parent plant |
| Position of suckers: close to parent growing (vertical growth) |
| Blotches at the petiole base: sparse blotching (FIG. 2) |
| Blotches colour: dark brown 10R3/2 |
| Petiole canal leaf III: wide with erect margins (FIG. 2) |
| Petiole margins: winged and not clasping the pseudostem (FIG. 2) |
| Wing type: dry |
| Petiole margin colour: 5R6/8 with greenish |
| Edge of the petiole margin: colourless (without a colour line along) |
| Petiole margin width: <1 cm |
| Leaf blade length: around 296.0 cm |
| Leaf blade width: around 84.0 cm |
| Leaf ratio: ≥3 (around 3.52) |
| Petiole length: 73.0 cm |
| Colour of leaf upper surface: 7.5GY4/2 (FIG. 3B) |
| Appearance of leaf upper surface: dull (FIG. 3B) |
| Colour of the leaf lower surface: 5GY5/4 (FIG. 3C) |
| Appearance of the leaf lower surface: dull (FIG. 3C) |
| Wax on leaves: moderately waxy |
| Insertion point of leave blades on petiole: asymmetric (FIG. 3A) |
| Shape of leave blade: both sides rounded (FIG. 3A) |
| Leaf corrugation: even, smooth |
| Colour of midrib dorsal surface: 2.5GY7/6 (FIG. 3B) |
| Colour of midrib ventral surface: between 5GY5/6 (FIG. 3C) |
| Colour of cigar leaf dorsal surface: 2.5GY6/6 (FIG. 4A) |
| Blotches on leaves of water suckers: without blotches (FIG. 4B) |
| Peduncle length: 47 cm |
| Empty nodes on peduncle: 1 |
| Peduncle width: 25.5 cm |

TABLE 1-continued

| Detailed descriptors |
|---|
| Peduncle colour: 5GY4/6 |
| Peduncle hairiness: very hairy, short hairs (similar to velvet touch) |
| Bunch Position: hanging vertically (bunch ready for harvest) |
| Bunch shape: Cylindrical (FIG. 5) |
| Bunch appearance: lax (one can easily place one's hand between the hands of fruit) (FIG. 5) |
| Flowers that form the fruit: female |
| Fruits: biseriate |
| Rachis type: present and male bud may be degenerated or persistent (FIG. 6) |
| Rachis position: falling vertically |
| Rachis appearance: neutral/male flowers on the whole stalk without persistent bracts |
| Male bud type: normal present (FIG. 6) |
| Male bud shape: lanceolate (FIG. 6) |
| Male bud size: length 23.2 cm and diameter 28.2 cm (at the widest section) |
| Bract base shape: large shoulder (FIG. 7A) |
| Bract apex shape: intermediate (FIG. 7C) |
| Bract imbrication: young bracts slightly overlap (FIG. 6) |
| Color of bract external face: 5R5/4 (FIG. 7A) |
| Colour of the bract internal face: 2.5Y8/6 in the upper section and 2.5RY6/8 near of the apex (FIG. 7B) |
| Colour on the bract apex: tinted with yellow |
| Colour stripes on bract: with discoloured lines on external face (FIG. 7A) |
| Bract scars on rachis: very prominent |
| Fading of colour on bract base: colour discontinuing towards the base (FIG. 7B) |
| Male bract shape: ovate x/y ≥ 0.28 (11.7/20 = 0.585) |
| Male bract lifting: lifting one at the time (FIG. 6) |
| Bract behavior before falling: revolute (rolling) (FIG. 6) |
| Wax on the bract: moderately waxy |
| Presence of grooves on the bract: moderate grooving (parallel bridges are distinguishable) |
| Male flower behavior: neutral/male flowers persistent |
| Compound tepal basic colour: cream 2.5Y8/2 (FIG. 8A) |
| Compound tepal pigmentation: very few or no visible sign of pigmentation (FIG. 8A) |
| Lobe colour of compound tepal: 2.5Y7/10 (FIG. 8B) |
| Lobe development of compound tepal: developed (FIG. 8B) |
| Free tepal colour: translucent (FIG. 8C) |
| Free tepal shape: oval (FIG. 8C) |
| Free tepal appearance: several folding under apex (FIG. 8C) |
| Free tepal apex development: developed (FIG. 8C) |
| Free tepal apex shape: thread-like (FIG. 8C) |
| Anther exertion: inserted (FIG. 8B) |
| Filament colour: white (FIG. 9) |
| Anther colour: 2.5Y8/4 |
| Pollen sac colour: 2.5Y7/4 |
| Style basic colour: white (FIG. 9) |
| Pigmentation on style: without pigmentation |
| Style exertion: inserted (FIG. 8B) |
| Style shape: straight (FIG. 10A) |
| Stigma colour: 2.5Y8/4 (FIG. 10A) |
| Ovary shape: slightly arched (FIG. 10B) |
| Ovary basic colour: white (FIG. 10B) |
| Ovary pigmentation: very few or no visible sign of pigmentation (FIG. 10B) |
| Dominant colour of male flower: cream (FIG. 11) |
| Arrangement of ovules: two rowed (FIG. 12) |
| Fruit position: curved upward 45° or more |
| Number of fruits: 16 fingers (FIG. 13) |
| Fruit length: 22.5 cm (FIG. 14A) |
| Fruit shape: straight in the distal part (FIG. 14A) |
| Transverse section of fruit: rounded (FIG. 14B) |
| Fruit apex: blunt-tipped (FIG. 14C) |
| Remains of flower relicts at fruit apex: base of the style prominent |
| Fruit pedicel length: 45 mm |
| Fruit pedicel width: 11 mm |
| Pedicel surface: hairless |
| Fusion of pedicels: very partially or no visible sign of fusion |
| Immature fruit peel colour: 2.5GY8/6 (FIG. 13) |
| Mature fruit peel colour: 2.5Y8/8 (FIG. 14) |
| Fruit peel thickness: 1 mm (FIG. 13) |
| Adherence of the fruit peel: fruit peels easily |
| Crack in fruit peel: cracked |

TABLE 1-continued

| Detailed descriptors |
|---|
| Pulp in fruit: with pulp |
| Pulp colour before maturity: 2.5Y8/6 |
| Pulp colour at maturity: cream 2.5Y8/4 (FIG. 14C) |
| Fruit fall from hands: deciduous |
| Flesh texture: soft |
| Predominant taste: sweet and acid |
| Presence of seeds with source of pollen: no |
| Seed surface: not applicable |
| Seed shape: not applicable |

TABLE 2

| Additional fruit, flowering, and harvest descriptors |
|---|
| Days for planting to first flowering: 286.75 |
| Number of leaves at flowering: 13 (first production cycle) |
| Number of leaves at harvest: 8 (first production cycle) |
| Days from flowering until harvest: 84 (first production cycle) |
| Bunch weight (Kg): 19.54 ($2^{nd}$ production cycle) |
| Number of hands: 7 ($2^{nd}$ production cycle) |
| Finger diameter (1/32"): 14 ($2^{nd}$ hand, $2^{nd}$ production cycle) |
| Ratooning from first to fourth production cycles: 223 days |
| Index of ratooning: 1.64 (average from first to fourth production cycle) |

What is claimed is:

1. A new and distinct banana plant having the characteristics substantially as described and illustrated herein.

* * * * *

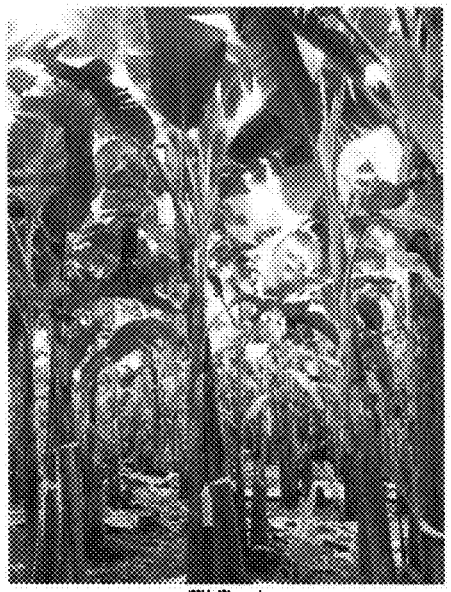
FIG. 1
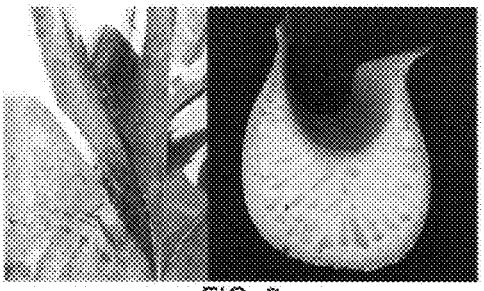
FIG. 2
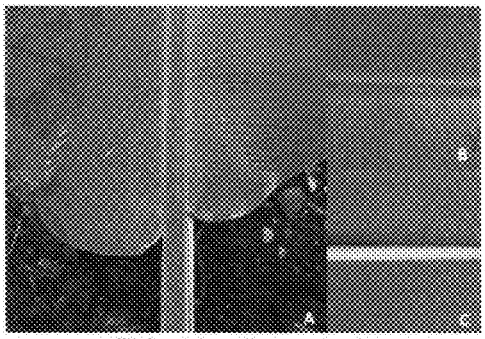
FIG. 3A, 3B, and 3C
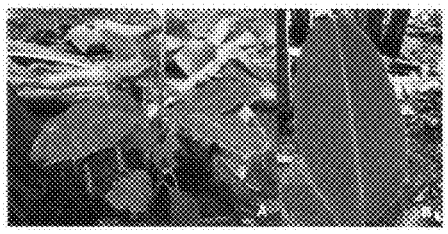
FIG. 4A & 4B
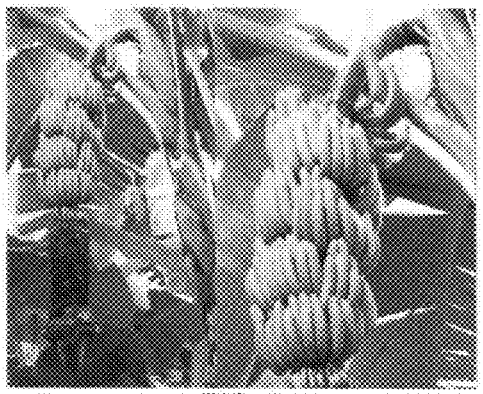
FIG. 5
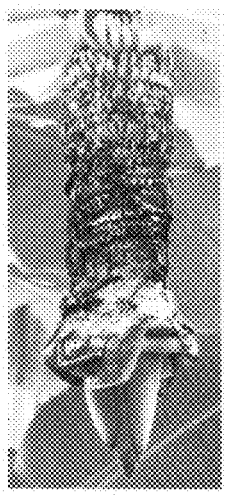
FIG. 6